(12) United States Patent
Merves

(10) Patent No.: US 7,329,264 B2
(45) Date of Patent: Feb. 12, 2008

(54) INSTRUMENT HANDLE FOR STORING SUTURE AND NEEDLES

(75) Inventor: Michael Merves, Naples, FL (US)

(73) Assignee: Arthrex, Inc., Naples, FL (US)

( * ) Notice: Subject to any disclaimer, the term of this patent is extended or adjusted under 35 U.S.C. 154(b) by 572 days.

(21) Appl. No.: 10/679,265

(22) Filed: Oct. 7, 2003

(65) Prior Publication Data
US 2004/0106935 A1 Jun. 3, 2004

Related U.S. Application Data

(60) Provisional application No. 60/416,265, filed on Oct. 7, 2002.

(51) Int. Cl.
*A61B 17/04* (2006.01)
*A61B 17/12* (2006.01)

(52) U.S. Cl. ..................................... 606/144

(58) Field of Classification Search ........ 606/144–150, 606/104, 139; 112/169; 289/13, 15, 17; 206/63.3, 63.5, 388–389, 398, 400
See application file for complete search history.

(56) References Cited

U.S. PATENT DOCUMENTS

| 3,103,666 | A | * | 9/1963 | Bone | 227/67 |
| 5,584,860 | A | * | 12/1996 | Goble et al. | 606/232 |
| 5,944,724 | A | * | 8/1999 | Lizardi | 606/104 |
| 6,136,010 | A | * | 10/2000 | Modesitt et al. | 606/144 |
| 2003/0204195 | A1 | * | 10/2003 | Keane et al. | 606/146 |

* cited by examiner

*Primary Examiner*—(Jackie) Tan-Uyen Ho
*Assistant Examiner*—Melanie Tyson
(74) *Attorney, Agent, or Firm*—Dickstein Shapiro LLP

(57) ABSTRACT

An instrument handle for storing of suture which can be easily accessed by a surgeon. The handle is provided with a cavity for housing sutures and needles. The cavity is accessed by opening a pivotable hatch. The suture is wrapped around a tie-down bar disposed on the inside of the pivotable hatch. If desired, a surgical needle may be attached to the suture and stored within a slot of the tie-down bar of the pivotable hatch.

20 Claims, 7 Drawing Sheets

INSTRUMENT HANDLE FOR STORING SUTURE AND NEEDLES

This application claims the benefit of U.S. Provisional Application Ser. No. 60/416,265, filed Oct. 7, 2002, the entire disclosure of which is incorporated by reference herein.

FIELD OF THE INVENTION

The present invention relates to the field of surgery and, more particularly, to an instrument handle for storing surgical suture and needles.

BACKGROUND OF THE INVENTION

The use of suture anchors and drivers for driving suture anchors into bone have come into widespread use in the surgical field. A suture anchor driver is typically formed of a cannulated tube attached to a cannulated handle and provided with a cleat on one side of the handle. The suture from the anchor is threaded through the cannulated driver and wrapped around the cleat. For rotation and installation of the suture anchor into the bone, a surgeon must first grasp and hold the handle with one hand and then, after the suture anchor is installed, unwrap or unwind the suture from the cleat to remove the driver and tie down the tissue to bone. The suture to be removed from the clear often becomes entangled or entwined, requiring unnecessary manipulation by the surgeon and decreasing the efficiency of the surgery. Moreover, the sterility of the suture, which is exposed to contaminants on the outside of the handle, can also be compromised during insertion of the suture anchor. If a needle is attached to the end of the suture, the needle is also exposed and can become unsterile or puncture the glove of the surgeon prior to use.

Accordingly, there is a need for an improved instrument handle for housing suture and for providing a reliable needle park that overcomes the deficiencies of the prior art. There is also a need for an instrument handle that stores suture and/or sutures attached to a surgical needle that is simple and inexpensive to manufacture, and that is easily accessed by a surgeon. A method of housing at least one strand of suture with or without an attached needle within the handle of an instrument, for installing a suture anchor into the bone, is also needed.

BRIEF SUMMARY OF THE INVENTION

The present invention overcomes the disadvantages of the prior art and fulfills the needs noted above by providing an instrument handle for storing of suture which can be easily accessed by a surgeon. The handle is provided with a cavity for housing sutures and needles. The cavity is accessed by opening a pivotable hatch. The suture is wrapped around a tie-down bar disposed on the inside of the pivotable hatch. If desired, a surgical needle may be attached to the suture and stored within a slot of the tie-down bar of the pivotable hatch.

Other features and advantages of the present invention will become apparent from the following description of the invention which refers to the accompanying drawings.

DETAILED DESCRIPTION OF THE INVENTION

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides an instrument handle for storing suture and/or suture attached to a surgical needle, which is simple to fabricate and which can be easily manipulated by a surgeon. As described in more detail below, the instrument handle is provided with a cavity for housing sutures and needles. The cavity is accessed by opening a pivotable hatch. The suture is wrapped around a tie-down bar disposed on the inside of the pivotable hatch and within the cavity.

Figure 1:
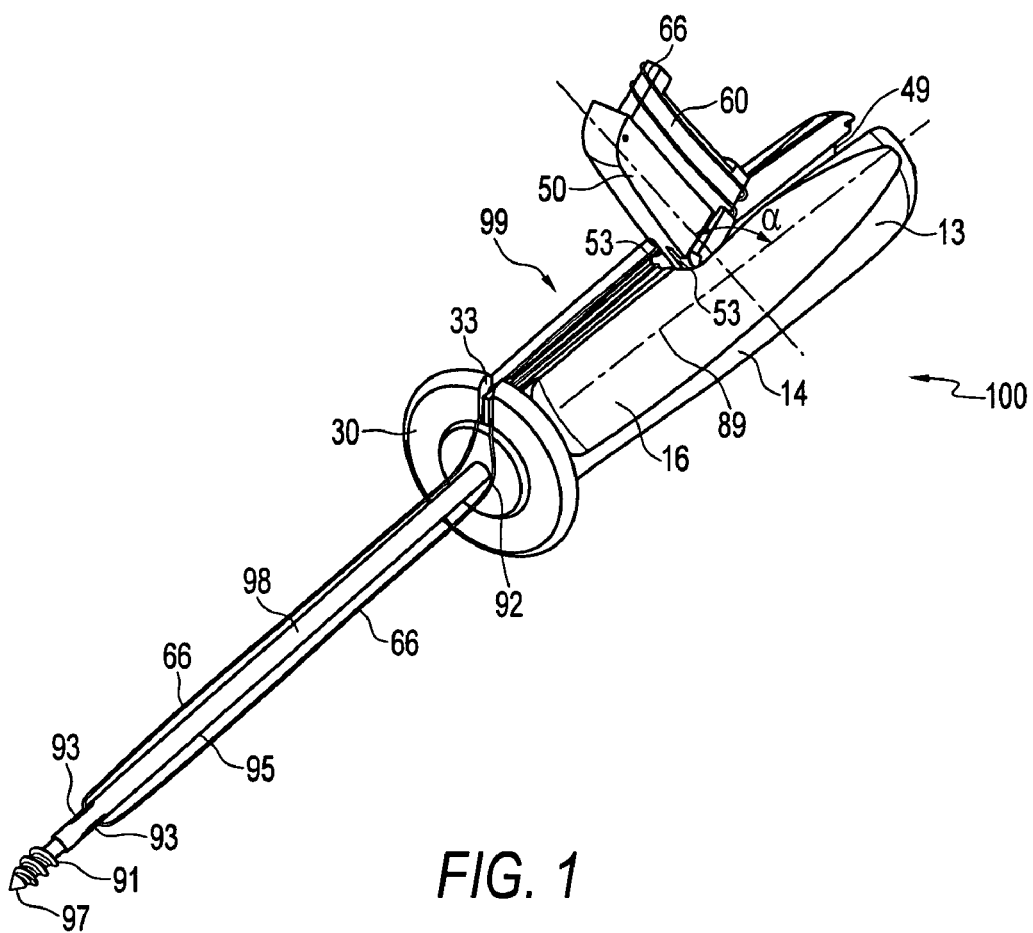
FIG. 1 illustrates an instrument handle according to the present invention.

Referring now to the drawings, where like elements are designated by like reference numerals, FIG. 1 illustrates an instrument 100 provided with handle 99 of the present invention. Instrument 100 comprises a cannulated elongated shaft 98 secured to handle 99 at its proximal end 92. A suture anchor 97, or any other anchoring device or implantable device attached to a suture, is provided at distal end 91 of the cannulated elongated shaft 98. Instrument 100 also comprises a cannula 67, illustrated in more detail in FIGS. 4 and 5, that extends through shaft 98 and handle 99 for receiving suture strands 66 attached to the suture anchor 97.

Figure 2:
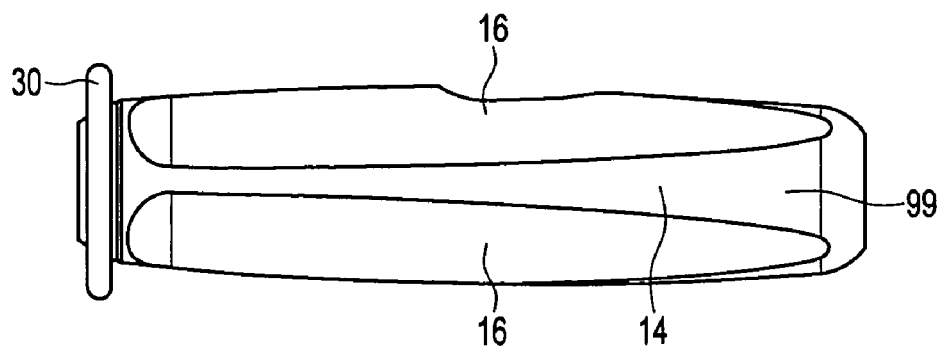
FIG. 2 illustrates a longitudinal perspective view of the instrument handle of FIG. 1.
Figure 3:
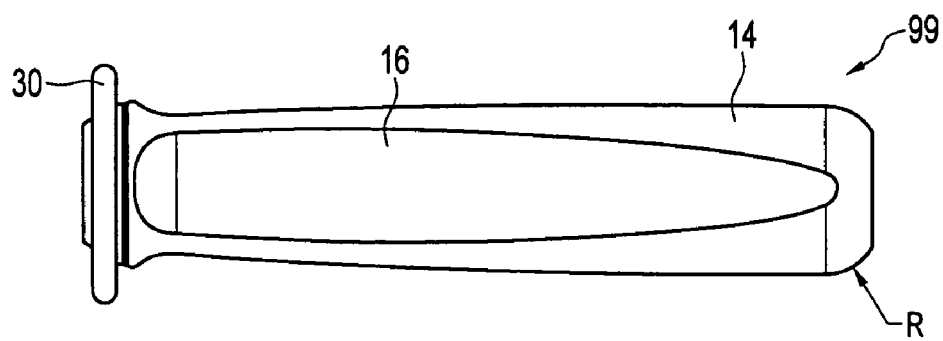
FIG. 3 illustrates another longitudinal perspective view of the instrument handle of FIG. 1.

As illustrated in FIGS. 2 and 3, the handle 99 of instrument 100 has an outer surface 13 provided with a grip formed of alternating raised edges 14 and depressions 16. In a preferred embodiment, the outer surface 13 is provided with a grip formed of four alternating raised edges 14 and four depressions 16. In this manner, a surgeon holding the handle can firmly grasp the instrument and, as described below, can easily access and manipulate the suture housed within the handle.

As shown in FIG. 1 and FIGS. 7-10, handle 99 of the present invention is provided with a cavity 49 for housing suture 66, or suture 66 attached to a needle 77. If desired, a plurality of sutures 66 with or without needles 77 may be housed within the housing cavity 49. The cavity 49 is accessed by opening a pivotable hatch 50. The suture 66 with or without needle 77 is wrapped around a tie-down bar 60 disposed on the inside of the pivotable hatch 50 and disposed within the housing cavity 49 when the hatch is closed. In this manner, the suture and/or the needles do not come in direct contact with external contaminants and are maintained sterile during the course of the surgery, until they are deployed.

Figure 6:
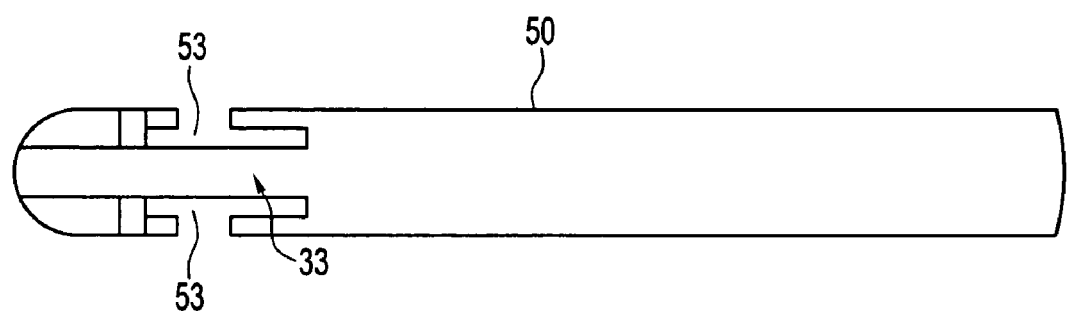
FIG. 6 illustrates a top view of the hatch of the instrument handle of FIG. 1.
Figure 7:
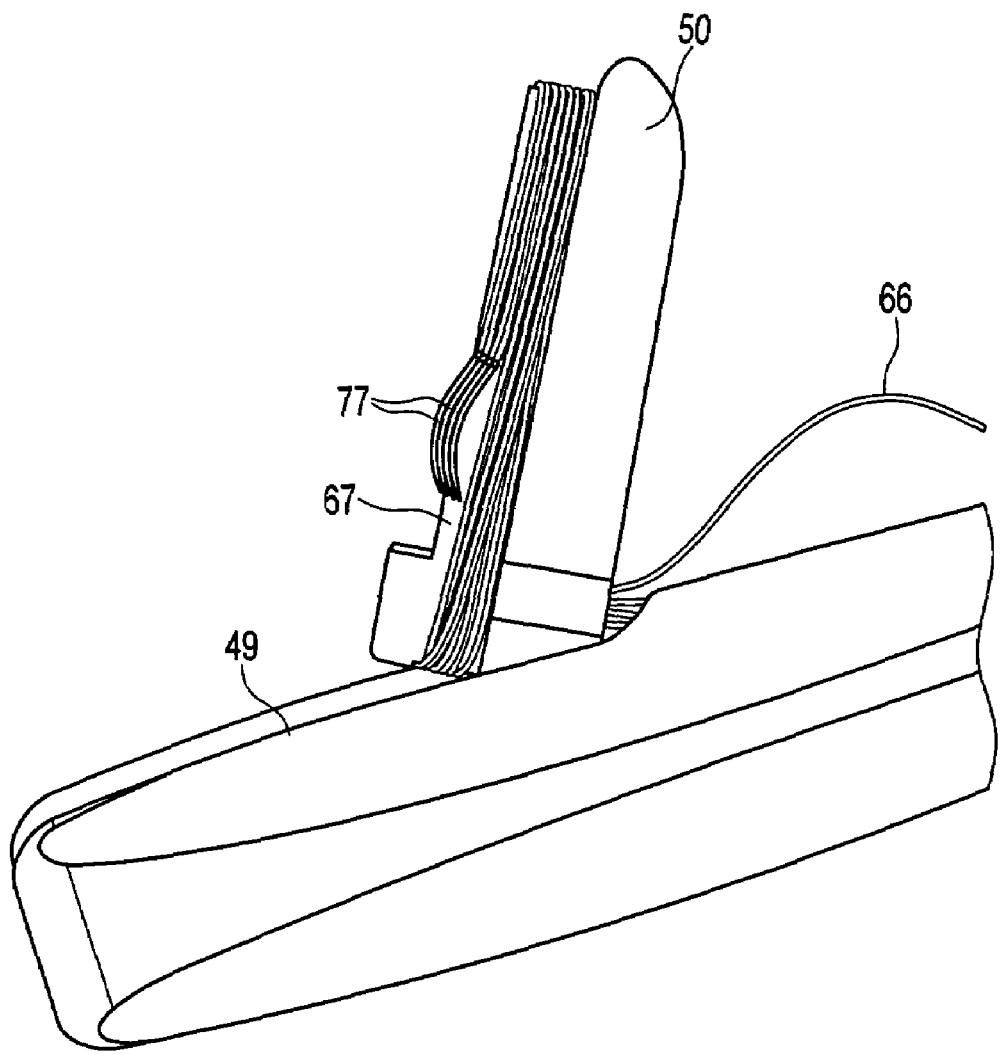
FIG. 7 illustrates a perspective view of the instrument handle of FIG. 1 provided with suture and in an open position.
Figure 8:
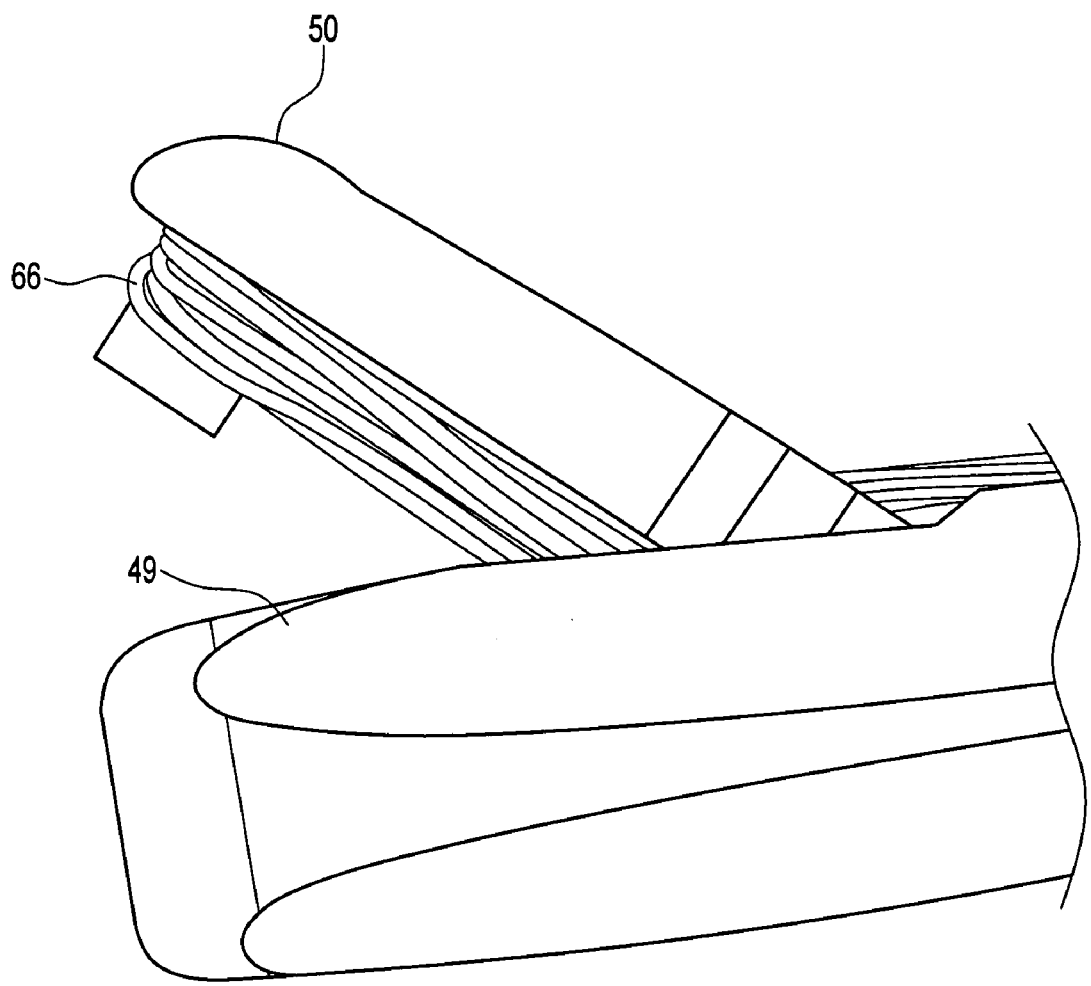
FIG. 8 illustrates a perspective view of instrument handle of FIG. 1 provided with suture and in another open position.
Figure 9:
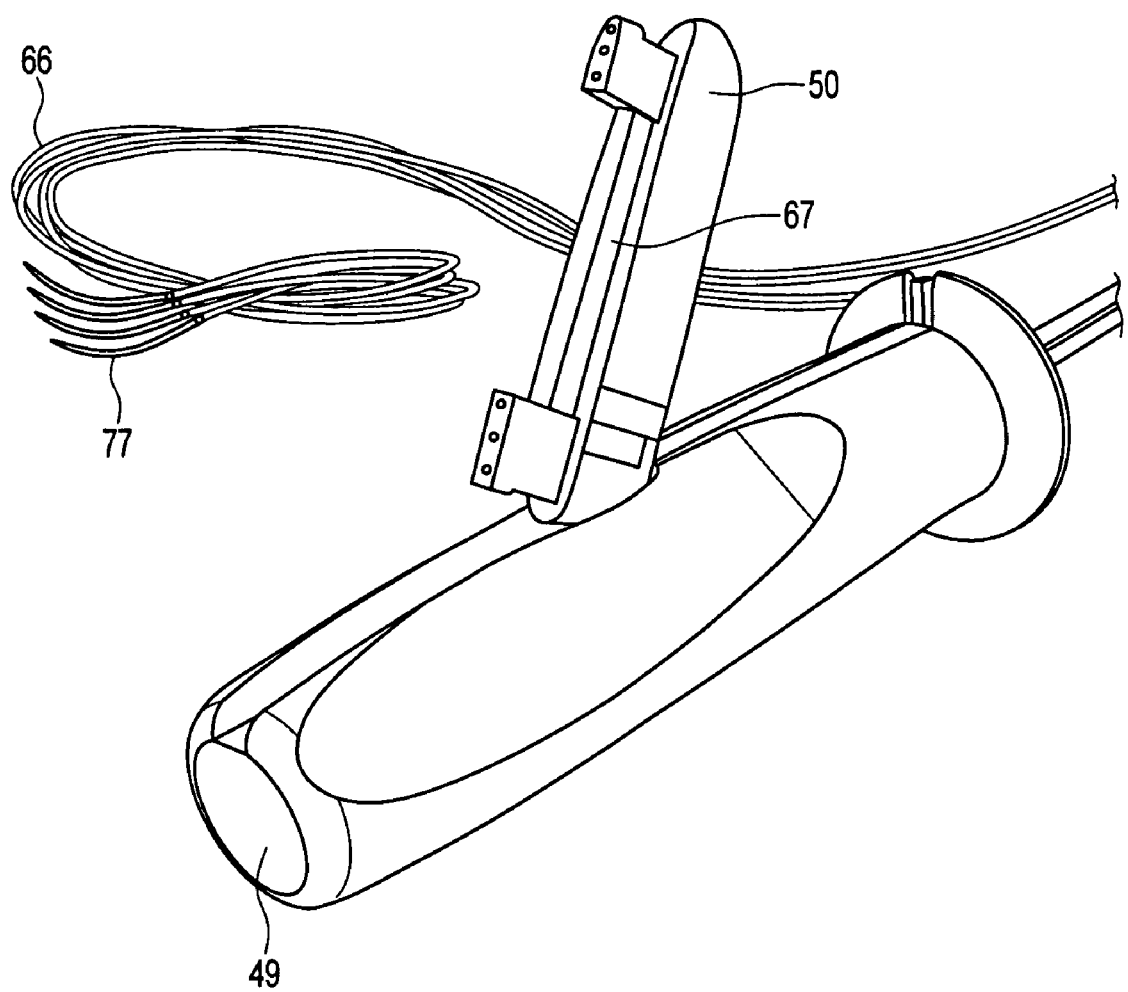
FIG. 9 illustrates a perspective view of the instrument handle of FIG. 1 provided with suture and needles and in an open position.
Figure 10:
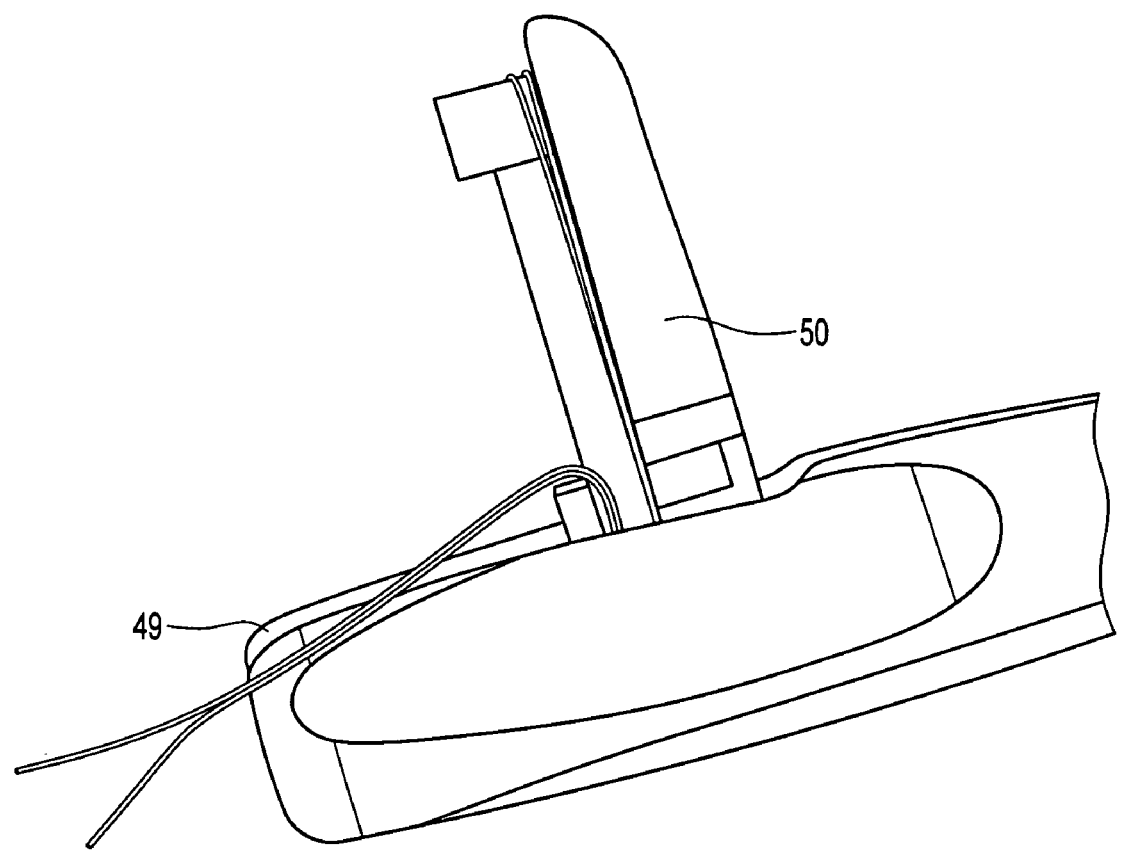
FIG. 10 illustrates another perspective view of the instrument handle of FIG. 1 provided with suture and in an open position.

A preferred method of operating handle 99 of instrument 100 in connection with the insertion of an anchoring device, for example, suture anchor 97 or other implantable device attached to a suture, in accordance with the present invention is described below with reference to FIGS. 1 and 7-10. FIG. 1 illustrates the suture anchor 97 attached to the distal end 91 of the cannulated elongated shaft 98 by suture strands 66. At the distal end 91, the suture strands 66 enter cannula 67 of the shaft 98 and then exit side orifices 93 of the cannulated elongated shaft 98 to extend along the longitudinal exterior surface 95 of the cannulated elongated shaft 98. The suture strands 66 further pass through U-shaped orifice 33 (FIG. 6) of circular plate 30 of the handle 99 and through two slots 53 (FIG. 6) of the pivotable hatch 50, to finally wrap around the tie-down bar 60 within the housing cavity 49. If desired, one or more of the suture strands 66 can be provided with an attached needle 77. As shown in FIG. 7, needles 77 are "parked" or secured within a slot 67 (FIGS. 7 and 9) of the tie-down bar 60. In this manner, various types of surgical needles, such as the surgical needle 77, may be safely stored within the handle 99, preventing therefore any piercing of surgical gloves and any problems in maintaining the needles sterile.

Figure 4:
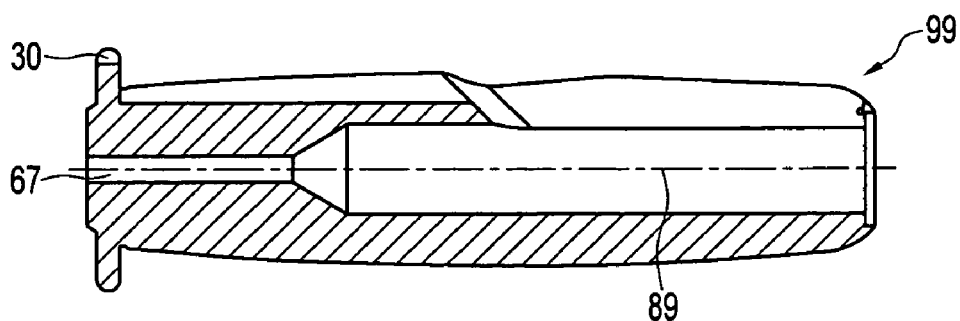
FIG. 4 illustrates a longitudinal cross-sectional view of the instrument handle of FIG. 1.
Figure 5:
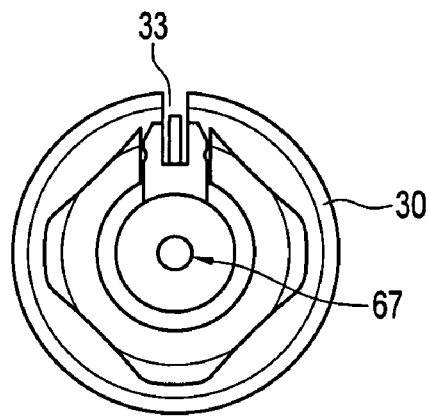
FIG. 5 illustrates a side view of the instrument handle of FIG. 1.

In use, the surgeon grasps the handle 99 with the pivotable hatch 50 in the "closed" position with sutures 66 wrapped around the tie-down bar 60 and, optionally, needles 77 stored within slot 67 of the tie-down bar 60, as shown in FIG. 4, for example. Subsequently, the surgeon uses his or her thumb to lift the pivotable hatch 50 of the instrument 100 to a desired opening position, such that the hatch 50 pivots relative to longitudinal axis 89 of the handle 99 by an angle "α" (FIG. 1) of about 10 degrees to about 170 degrees. For example, FIGS. 7-10 illustrate the pivotable hatch 50 open at about 120 degrees (FIG. 7), at about 45 degrees (FIG. 8), at about 140 degrees (FIG. 9) and at about 90 degrees (FIG. 10), respectively. The surgeon then pulls out the desired suture 66 with or without attached needle 77 from around the tie-down bar 60 and from within the slot 67 of the handle 99. In this manner, twisting and entangling of the sutures is avoided prior to use. The sutures and the needles are also maintained sterile, as they are stored within the handle and not wrapped exteriorly and around a cleat and in contact with contaminants, as in the prior art devices.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A suture storing device, comprising:
   an elongated shaft having a longitudinal axis, a proximal end and a distal end;
   a handle provided at the proximal end; and
   a cavity within the handle for storing at least one strand of suture, wherein the cavity is provided with a hatch, the hatch having a tie-down bar attached to its inside and integral to the hatch for storing at least one strand of suture wrapped around the tie-down bar, the hatch being configured to pivot, together with the tie-down bar on its inside, relative to the longitudinal axis of the elongated shaft.

2. The suture storing device of claim 1, wherein the hatch forms an angle with respect to the longitudinal axis of the elongated shaft.

3. The suture storing device of claim 2, wherein the hatch forms a zero degree angle with respect to the longitudinal axis of the elongated shaft when the hatch is in a closed position.

4. The suture storing device of claim 2, wherein the angle is different from a zero degree angle with respect to the longitudinal axis of the elongated shaft when the hatch is in an opened position.

5. The suture storing device of claim 4, wherein the angle is of about 10 degrees to about 170 degrees with respect to the longitudinal axis of the elongated shaft.

6. The suture storing device of claim 1, wherein the at least one strand of suture is further provided with a needle.

7. The suture storing device of claim 1, wherein the elongated shaft is configured to accommodate an implantable device.

8. The suture storing device of claim 7, wherein the implantable device is a suture anchor or an implant.

9. A device for housing sutures attached to surgical needles, comprising:
   an elongated shaft having a longitudinal axis, a proximal end and a distal end;
   a handle provided at the proximal end; and
   a cavity within the handle for storing at least one strand of suture provided with at least one surgical needle, the cavity being provided with a pivotable hatch, the pivotable hatch having a tie-down bar attached to its inside and integral to the hatch, the pivotable hatch being configured to pivot, together with the tie-down bar on its inside, relative to the longitudinal axis of the elongated shaft;
   wherein the tie-down bar is further provided with a slot for storing the at least one surgical needle; and
   wherein the pivotable hatch is configured to be integral with the handle when the pivotable hatch is in a closed position.

10. The device of claim 9, wherein the at least one strand of suture provided with the at least one surgical needle is stored within the handle when the pivotable hatch is in the closed position.

11. The device of claim 10, wherein the at least one strand of suture provided with the at least one surgical needle is wrapped around the tie-down bar when the pivotable hatch is in the closed position.

12. The device of claim 9, wherein the pivotable hatch is not integral with the handle when the pivotable hatch is in an opened position.

13. The device of claim 12, wherein the pivotable hatch forms an angle with respect to the longitudinal axis of the elongated shaft when the pivotable hatch is in the opened position.

14. The device of claim 13, wherein the angle is of about 10 degrees to about 170 degrees with respect to the longitudinal axis of the elongated shaft.

15. The device of claim 9, wherein the elongated shaft is configured to accommodate an implantable device.

16. The device of claim 15, wherein the implantable device is a suture anchor or an implant.

17. A method of dispensing a surgical suture, comprising the steps of:
providing a suture housing device comprising: a cannulated elongated shaft having a longitudinal axis, a proximal end and a distal end; a handle provided at the proximal end; and a cavity within the handle for storing at least one strand of suture, the cavity being provided with a pivotable hatch, the pivotable hatch having a tie-down bar attached to its inside and integral to the hatch, the pivotable hatch being configured to pivot, together with the tie-down bar on its inside, relative to the longitudinal axis of the shaft, the pivotable hatch being integral with the handle when the pivotable hatch is in a closed position, and wherein the surgical suture is coiled around the tie-down bar;

actuating the pivotable hatch so that the pivotable hatch forms an angle with respect to the longitudinal axis of the elongated shaft; and deploying the surgical suture from around the tie-down bar.

18. The method of claim 17, further comprising the step of attaching a surgical needle to the surgical suture.

19. The method of claim 18, further comprising the step of attaching an implantable device to the surgical suture.

20. The method of claim 17, wherein the angle is of about 10 degrees to about 170 degrees with respect to the longitudinal axis of the elongated shaft.

* * * * *